(12) United States Patent
Burstein et al.

(10) Patent No.: US 10,449,342 B2
(45) Date of Patent: Oct. 22, 2019

(54) MEDICAL APPLICATOR

(71) Applicant: INNOVATIVE PHARMACEUTICAL CONCEPTS (IPC) INC, Road Town (VG)

(72) Inventors: Pinchas Burstein, Ramat Hasharon (IL); Joshua Altman, Tel Aviv (IL); Moshe Tshuva, Tel Aviv (IL)

(73) Assignee: INNOVATIVE PHARMACEUTICAL CONCEPTS (IPC) INC., Road Town (VG)

( * ) Notice: Subject to any disclaimer, the term of this patent is extended or adjusted under 35 U.S.C. 154(b) by 443 days.

(21) Appl. No.: 14/429,593

(22) PCT Filed: Sep. 15, 2013

(86) PCT No.: PCT/IL2013/050783
§ 371 (c)(1),
(2) Date: Mar. 19, 2015

(87) PCT Pub. No.: WO2014/045277
PCT Pub. Date: Mar. 27, 2014

(65) Prior Publication Data
US 2015/0246212 A1    Sep. 3, 2015

Related U.S. Application Data

(60) Provisional application No. 61/702,752, filed on Sep. 19, 2012.

(51) Int. Cl.
*A61M 35/00* (2006.01)
*A61K 31/19* (2006.01)
*A61M 5/315* (2006.01)

(52) U.S. Cl.
CPC .......... *A61M 35/003* (2013.01); *A61K 31/19* (2013.01); *A61M 5/3158* (2013.01)

(58) Field of Classification Search
CPC .... A61M 35/003; A61M 5/3153; A61K 31/19
See application file for complete search history.

(56) References Cited

U.S. PATENT DOCUMENTS 3,715,060 A    2/1973  Benson
4,583,982 A *  4/1986  Vlock ................. A61M 35/003
                                                       222/575

(Continued)

FOREIGN PATENT DOCUMENTS

WO    2003028623 A2    4/2003

OTHER PUBLICATIONS

Ustine, Richard and Marcela Riojas, "Diagnosis and Management of Contact Dermatitis" American Family Physician, Aug. 1, 2010, <http://www.aafp.org/afp/2010/0801/p249.pdf> accessed Jun. 9, 2017.*

(Continued)

*Primary Examiner* — Tatyana Zalukaeva
*Assistant Examiner* — Gabriella E Burnette

(57) ABSTRACT

An applicator for administration of a medicament comprises a container in fluid communication with a dispenser having a plurality of non-deformable structures configured for retaining a predetermined volume of a liquid medicament delivered from the container. The dispenser is capable of delivering at least a part of said predetermined volume of said liquid medicament to a surface upon contact therewith.

14 Claims, 5 Drawing Sheets

(56) References Cited

U.S. PATENT DOCUMENTS

| | | | |
|---|---|---|---|
| 5,308,343 A | | 5/1994 | Gafner |
| 5,851,079 A | * | 12/1998 | Horstman ............ A45D 34/042 |
| | | | 401/174 |
| 2004/0186183 A1 | | 9/2004 | Johnson |
| 2007/0110506 A1 | * | 5/2007 | Erickson ................ A45D 34/04 |
| | | | 401/205 |
| 2007/0161964 A1 | * | 7/2007 | Yuzhakov ......... A61M 37/0015 |
| | | | 604/272 |
| 2009/0192442 A1 | * | 7/2009 | Ignon .................. A61M 35/003 |
| | | | 604/22 |
| 2012/0064139 A1 | * | 3/2012 | McGrath ........... A61F 13/00063 |
| | | | 424/407 |
| 2013/0144221 A1 | | 6/2013 | Burstein et al. |

OTHER PUBLICATIONS

Merriam-Webster definition of abrade https://www.merriam-webster.com/dictionary/abrade.*

Merriam-Webster Dictionary definition of Actuate, https://www.merriam-webster.com/dictionary/actuate.*

Israeli Patent Office, "International Search Report and Written Opinion in corresponding International Application No. PCT/IL2013/050783", dated Sep. 15, 2013, Israel.

* cited by examiner

MEDICAL APPLICATOR

FIELD AND BACKGROUND OF THE INVENTION

The present invention relates to medical delivery devices and, more particularly, to an applicator useful for the treatment of skin lesions.

Most skin lesions are benign and do not pose a health risk and as such are typically removed for aesthetic reasons using cryosurgery, lasers or surgical excision. Larger skin lesions or suspected cancerous lesions which require precise removal and histologic analysis are typically removed via surgical excision.

Pharmaceutical compositions that can be used to remove skin lesions are known in the art. For example, international patent application WO 03/028623 describes a pharmaceutical composition that can be used to effectively remove skin lesions while maintaining lesion tissue preserved for subsequent histological analysis. Such a pharmaceutical composition is advantageous in that it enables non-surgical removal of a lesion while preserving lesion tissue cellular architecture.

Topical applicators such as the one described in, for example, U.S. patent application Ser. No. 13/816,380 can be used to deliver the aforementioned pharmaceutical compositions. However, such applicators cannot provide the coverage and dosing accuracy required for safe and effective treatment of skin lesions.

In order to traverse these limitations, the present inventors devised an applicator that can be used to apply an accurate dose of a tissue-ablative composition to the target skin lesion tissue, in sufficient amount to effectively remove the skin lesion tissue, while minimizing exposure of surrounding healthy tissue to the ablative composition.

SUMMARY OF THE INVENTION

According to one aspect of the present invention there is provided an applicator for administration of a medicament. The applicator includes a container being in fluid communication with a dispenser having a plurality of non-deformable structures configured for retaining a predetermined volume of a liquid medicament delivered from the container. The dispenser is capable of delivering at least a part of the predetermined volume of the liquid medicament to a surface upon contact therewith.

According to another aspect of the present invention there is provided a method of treating a skin lesion. The method includes the steps of (i) communicating a predetermined volume of a liquid medicament from a container to a fluidly-coupled dispenser having a plurality of non-deformable structures configured for retaining the predetermined volume of a liquid medicament; and (ii) contacting the dispenser with the skin lesion thereby delivering at least a part of the predetermined volume of the liquid medicament to the skin lesion.

According to further features in preferred embodiments of the invention described below, the plurality of non-deformable structures are configured for retaining the predetermined volume of a liquid medicament via capillary forces.

According to still further features in the described preferred embodiments the delivery of at least said part of the predetermined volume of the medicament to the surface upon contact therewith is effected via capillary transfer.

According to still further features in the described preferred embodiments the plurality of non-deformable structures are grooves or cavities.

According to still further features in the described preferred embodiments a tissue-contacting surface of the dispenser is configured for tissue penetration or disruption.

According to still further features in the described preferred embodiments the applicator further includes a mechanism configured for actuating release of the predetermined volume of the medicament from the container to the dispenser.

According to still further features in the described preferred embodiments the predetermined volume of the medicament is between about 1 μL to about 100 μL.

According to still further features in the described preferred embodiments the predetermined volume of the medicament is about 5 μL.

According to still further features in the described preferred embodiments the container is a deformable container.

According to still further features in the described preferred embodiments the applicator further includes the medicament within the container.

According to still further features in the described preferred embodiments the medicament includes trichloroacetic acid.

According to still further features in the described preferred embodiments the medicament further includes formic acid.

According to still further features in the described preferred embodiments the method of treating a skin lesion further includes a step of forcibly pressing the dispenser on the skin lesion to thereby facilitate penetration of the medicament into the skin lesion tissue.

According to still further features in the described preferred embodiments the skin lesion is a benign or a malignant skin lesion.

According to still further features in the described preferred embodiments the skin lesion is selected from a group consisting of seborrheic keratosis, actinic keratosis, intradermal nevus, verucae, condylomata acuminata, seborrheic dermatitis, atopic dermatitis, eczema, hyperkeratosis, acne (acne vulgaris) and psoriasis.

The present invention successfully addresses the shortcomings of the presently known configurations by providing a novel applicator capable of providing a liquid medicament to a target skin lesion accurately, safely and effectively.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
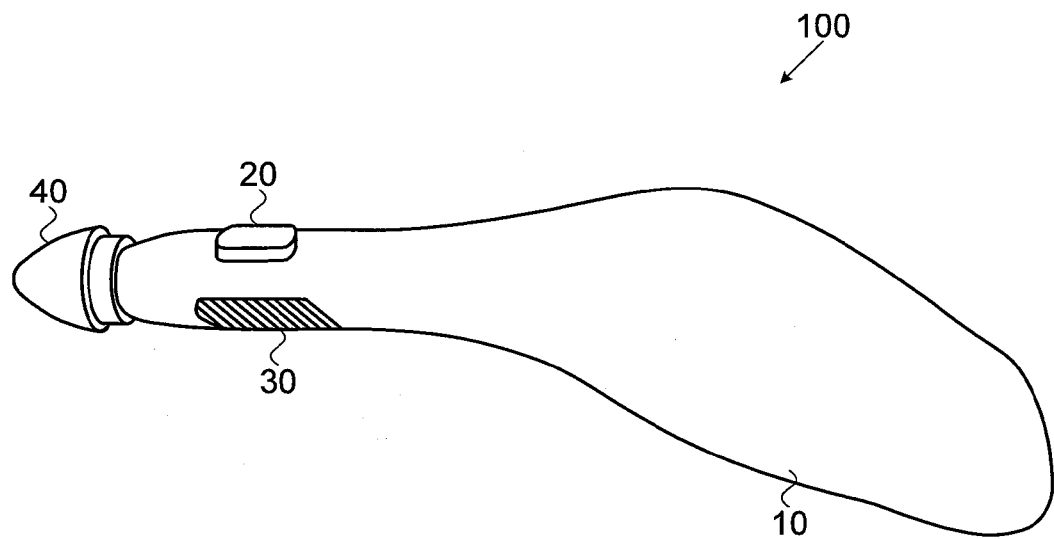
FIG. 1 is an isometric illustration of a preferred applicator.

The present invention relates to a medicament applicator and in particular, to a medicament applicator having a dispenser capable of delivering an accurate, area-constrained dose of a medication upon contact with a tissue surface.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Devices for delivering a medication from a porous dispenser head (e.g. foam head) are known in the art. The dispenser of such devices typically traps a medication within the pores of a compressible matrix such as an open cell foam, and delivers the medication to the skin when forcibly compressed against the skin to deform/compress the medicament-containing pores (essentially squeezing out the medication from the pores). In such devices the volume of medication delivered varies with the force applied to the dispenser while compression of the dispenser can lead to runoff of excessive amount of the medication and exposure of non-target tissues to a potentially harmful medication.

While reducing the present invention to practice, the present inventor devised a dispenser head that it capable of accurate and reproducible delivery of a predetermined volume of medication to a target skin region safely without medication runoff.

Thus, according to one aspect of the present invention there is provided an applicator for administration of a medicament.

The applicator includes a container for holding a liquid medicament and is in fluid communication with a dispenser having a plurality of non-deformable structures configured for retaining a predetermined volume of a liquid medicament delivered from the container.

The dispenser is capable of delivering at least a part of the predetermined volume of the liquid medicament to a surface of a skin lesion upon contact therewith.

As is further described hereinbelow, the present device is preferably configured as a pen applicator with the container being in fluid communication with a dispenser having grooves/channels on the tissue contact surface thereof. The medicament delivered from the container to the dispenser is trapped in the grooves/channels under capillary forces and is released via capillary transfer when the tissue-contacting surface of the dispenser comes into contact with the tissue. To facilitate penetration of the medicament into the treated tissue, the dispenser optionally also includes tissue-disrupting/penetrating structures.

As used herein, the phrase "non-deformable", when used with respect to medicament-retaining structures, refers to structures that do not appreciably deform when the dispenser is applied to a tissue.

The term "medicament" used herein refers to any pharmaceutical composition or drug which may be used for treating skin disorders, including but not limited to, compositions capable of causing drying (mummification) and separation of a skin lesion tissue.

The phrase "skin lesion" used herein refers to a benign or a malignant skin lesion such as, but not limited to, seborrheic keratosis, actinic keratosis, intradermal nevus, verucae, condylomata acuminata, seborrheic dermatitis, atopic dermatitis, eczema, hyperkeratosis, acne (acne vulgaris) and psoriasis.

The plurality of non-deformable structures for retaining a predetermined volume of liquid medicament on the surface of the dispenser by capillary forces can be, for example, grooves, channels or cavities or any open-ended structures that enable capillary transfer of the medicament upon contact between the dispenser and a tissue. The structures are preferably configured such that a medicament can be trapped therein under capillary forces and yet is maximally exposed to a tissue surface for capillary transfer. In that respect, a groove or channel which is exposed lengthwise to a tissue maximizes surface contact between the medicament and tissue.

Capillary transfer of the liquid medicament can be effected at the point of contact delicately without forcing out (e.g., ejecting or squeezing) the liquid medicament, thereby avoiding runoff and exposure of a non-target healthy tissue to the medicament.

Preferably the structures of the dispenser are rigid enough not to deform under the pressure of application (which can be anywhere from 50-500 grams). By maintaining their shape during delivery, the structures facilitate penetration of the medicament being applied to sufficient depth of the skin lesion tissue.

Hence, the applicator of the present invention is uniquely capable of delivering a liquid medicament to a target skin lesion accurately, safely and effectively.

Reference is now made to FIGS. 1-9 which illustrate a preferred embodiment of the present applicator which is referred to as applicator 100.

FIG. 1 illustrates an isometric view of applicator 100. Applicator 100 includes a housing 10 provided with an actuating button 20 and gripping pads 30. Applicator 100 further includes a protective cap 40 for covering a dispenser 80 (shown in FIG. 2). Housing 10 is ergonomically shaped for comfortable grip and single-handed (both left handed and right handed) operation. It will be understood however, that other shapes, e.g. cylindrical etc are can also be used with the present invention without detracting from its intended functionality.

Housing 10 can be made of any suitable plastic or other moldable polymer material, preferably polycarbonate. Actuating button 20 and gripping pads 30 are preferable made of polycarbonate, ethylene-vinyl acetate (EVA) or a thermoplastic elastomer (TPE).

Figure 2:
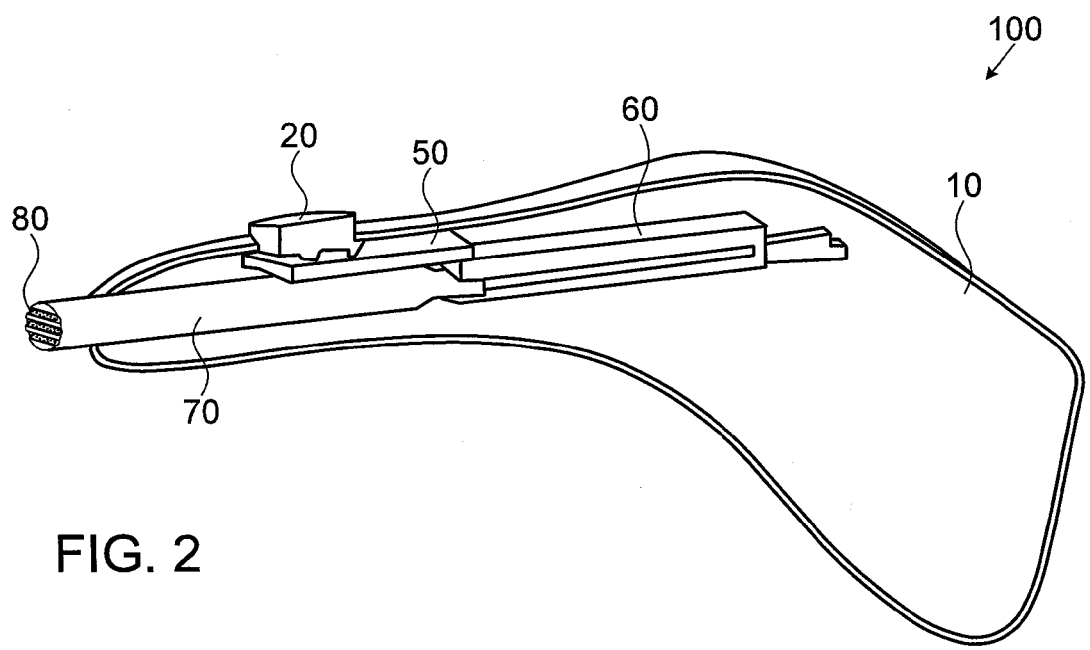
FIG. 2 is a cross-sectional illustration of the applicator from FIG. 1.

FIG. 2 illustrates a cross-sectional view of applicator 100 showing container 70 and fluidly connected dispenser 80. Container 70 is preferably made of flexible and squeezable, preferably acid resistant material for enabling delivery of liquid medicament accommodated in the container to dispenser 80. The phrase "acid resistant material" used herein refers to a material capable of remaining essentially unaffected by exposure to strong acids having a pH of 1 at room temperature for one month period. Suitable flexible and squeezable acid-resistant material can be, for example, fluorinatedethylenepropylene (FEP), polytetrafluoroethylene (PTFE), polyvinylidene fluoride (PVDF), or polypropylene (PP). In some embodiments, container 70 has a capacity to hold between about 50 μL and about 1,000 μL, preferably about 500 μL of liquid medicament.

Actuating button 20, drawing bar 50 and rack 60 are components of a preferred mechanism for the release of a predetermined volume of liquid medicament from container 70 to dispenser 80. Rack 60 is provided with a toothed upper surface and a smooth lower surface. Upon pressing actuating button 20, a spring-loaded drawing bar 50 drags the upper (toothed) surface of rack 60, thereby squeezing the bottom edge of container 70 between the upper and lower surfaces of rack 60. Consequently, upon each actuation of button 20 a specific volume of the liquid medicament is delivered to the surface of dispense 80. The volume can be adjusted based on the type and size of the target skin lesion, preferably ranging between 4 and 10 μL.

Dispenser 80 is preferably made of polycarbonate. Drawing bar 50 and rack 60 are preferably made of polycarbonate, ethylene-vinyl acetate (EVA) or a thermoplastic elastomer (TPE).

Numerous types of liquid medicaments can be used with applicator 100. Preferably, the liquid medicament comprises trichloroacetic acid (TCA) suitable for removal of skin tissue. In another embodiment the liquid medicament comprises a mixture of TCA and formic acid suitable for removal and preservation of skin tissue such as described, for example, in U.S. patent application Ser. No. 13/816,380.

Figure 3:
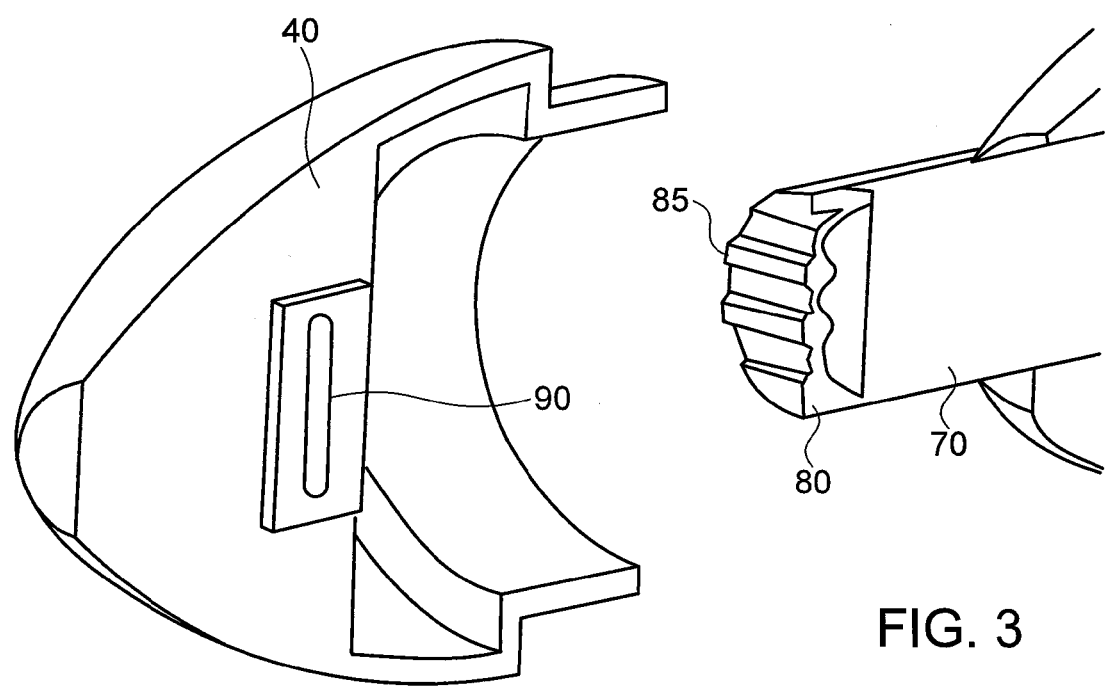
FIG. 3 is a cross-sectional illustration of the distal end of the applicator from FIG. 3 in which the protective cap is removed.

FIG. 3 illustrate a cross-sectional view of protective cap 40 and dispenser 80 of applicator 100. Protective cap 40 includes member 90 which is releasably connected to dispenser 80 (preferably via a tear/break-off connection). Dispenser 80 which is in fluid communication with container 70 includes a plurality of (non-deformable) structures 85 sized and configured for retaining a liquid medicament via capillary forces.

The phrase "capillary forces" used herein refers to the attraction of molecules of the liquid to molecules of the surrounding solid. Accordingly, the plurality of structures 85 of applicator 100 of the present invention are configured for retaining a specific volume of liquid medicament solely by capillary forces and without the assistance of any external forces such as gravity. The dispenser loaded with liquid medicament can be placed on a specific target skin location safely without risking a non-intentional release or spillage of a potentially toxic medicament on a non-target healthy tissue. Upon contact with a skin surface the liquid medicament is transferred to the skin tissue via capillary transfer delicately and safely.

Figure 4:
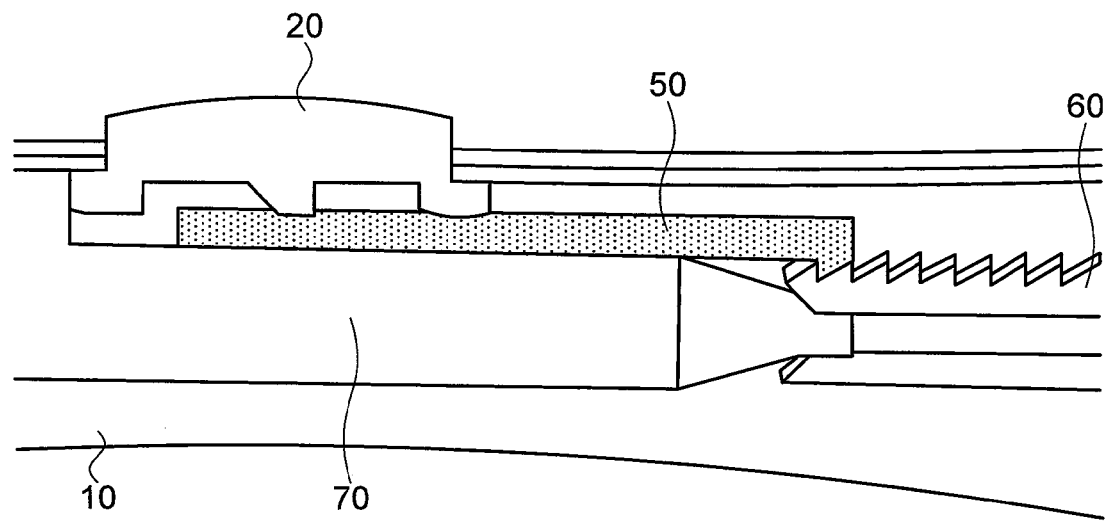
FIG. 4 is a cross-sectional illustration of the applicator from FIG. 2 in which the mechanism for actuating release of medicament is presented.
Figure 5:
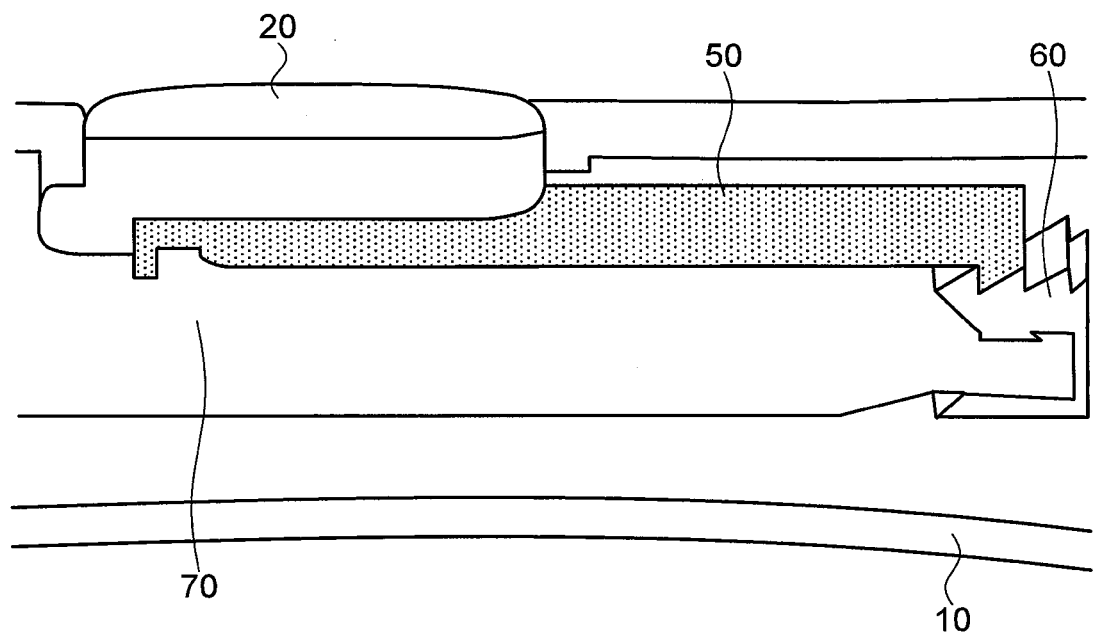
FIG. 5 is a cross-sectional illustration the applicator from FIG. 4 in which the mechanism for actuating release of medicament is presented in an enlarged view.
Figure 6:
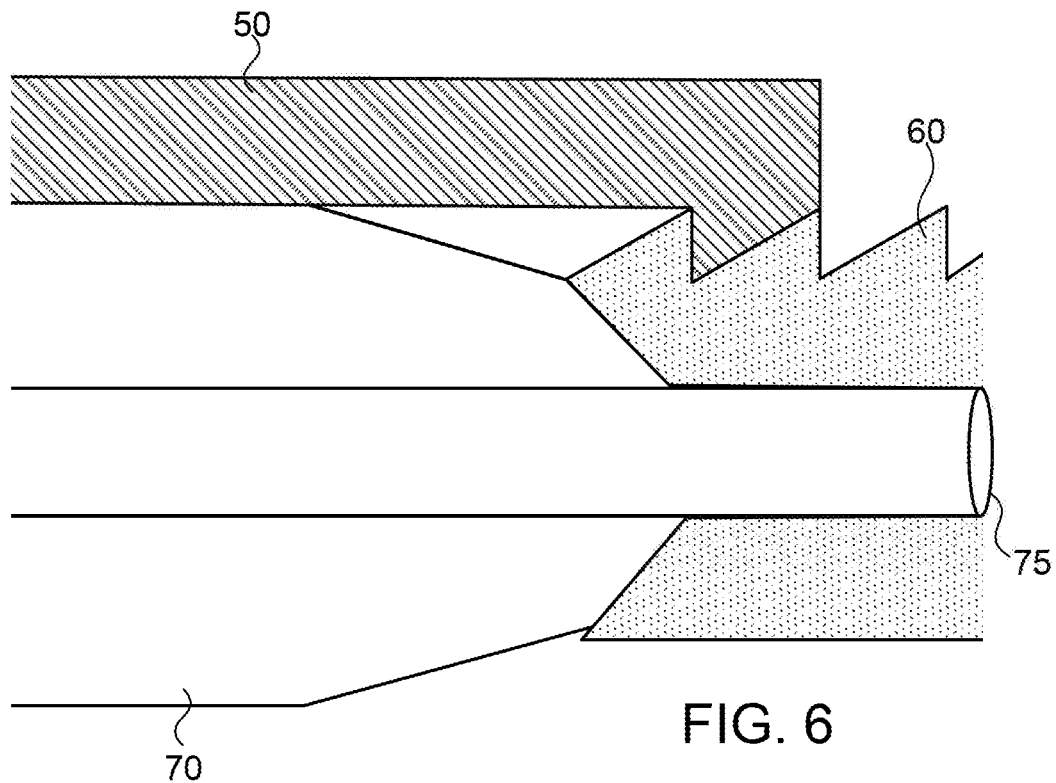
FIG. 6 is a cross-sectional illustration the applicator from FIG. 5 in which the proximal end of the mechanism for actuating release of medicament is presented in an enlarged view.

FIGS. 4-6 illustrate a cross-sectional view of a preferred mechanism for actuating release of a liquid medicament. Housing 10 is provided with container 70, actuating button 20, drawing bar 50 and rack 60. Container 70 is preferably made of flexible and squeezable material for enabling delivery of liquid medicament from container 70 to dispenser 80. Container 70 is preferably provided with rib 75 (shown in FIG. 6) to improve consistency of delivery. Rack 60 is provided with a toothed upper surface and a smooth lower surface. Upon pressing actuating button 20, spring-loaded drawing bar 50 drags the toothed upper surface of rack 60, thereby squeezing the bottom edge of container 70 between the upper and lower surfaces of rack 60. Consequently, upon each press of actuating button 20 a predetermined volume of the liquid medicament is transferred from container 70 to the surface of dispenser 80 where it is retained by capillary forces, as described hereinabove.

Figure 7:
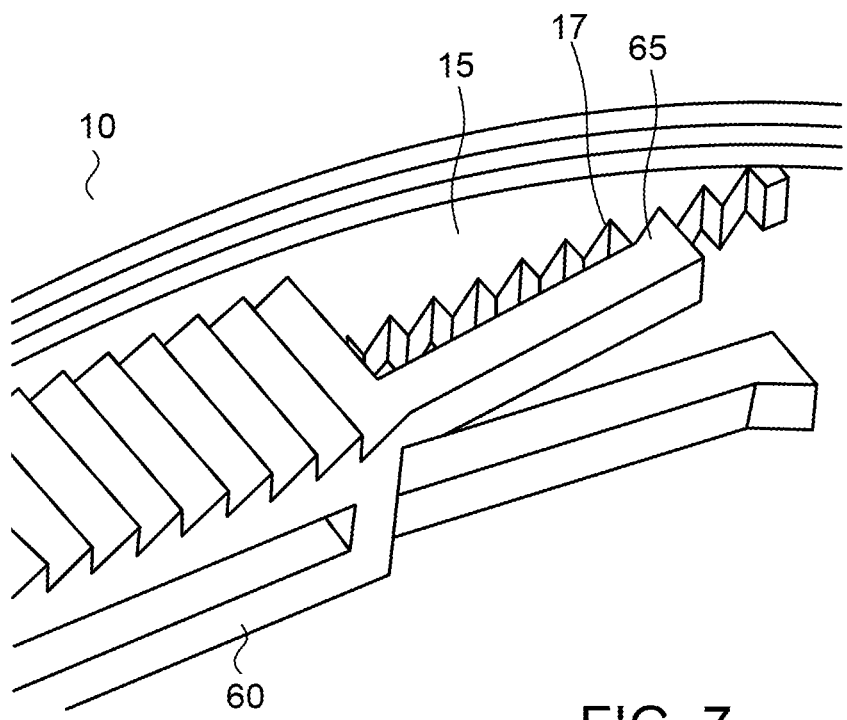
FIG. 7 is a cross-sectional illustration of the applicator from FIG. 2 in which the locking mechanism for preventing backflow of medicament is presented in an enlarged view.

FIG. 7 illustrates a cross-sectional view of a preferred mechanism for preventing rack 60 from moving backwards following release of medicament. Rack 60 is provided with a flexible arm 65 which is in an operative relation with an inner toothed surface 15 of housing 10. Rack 60 is dragged in a distal direction by drawing bar 50 (shown in FIGS. 4-6). When actuating button 20 (shown in FIGS. 4-5) is released, arm 65 rides over to the next notch 17 of inner surface 15, thereby preventing rack 60 from moving backwards, thus preventing any backflow of the medicament.

Figure 8:
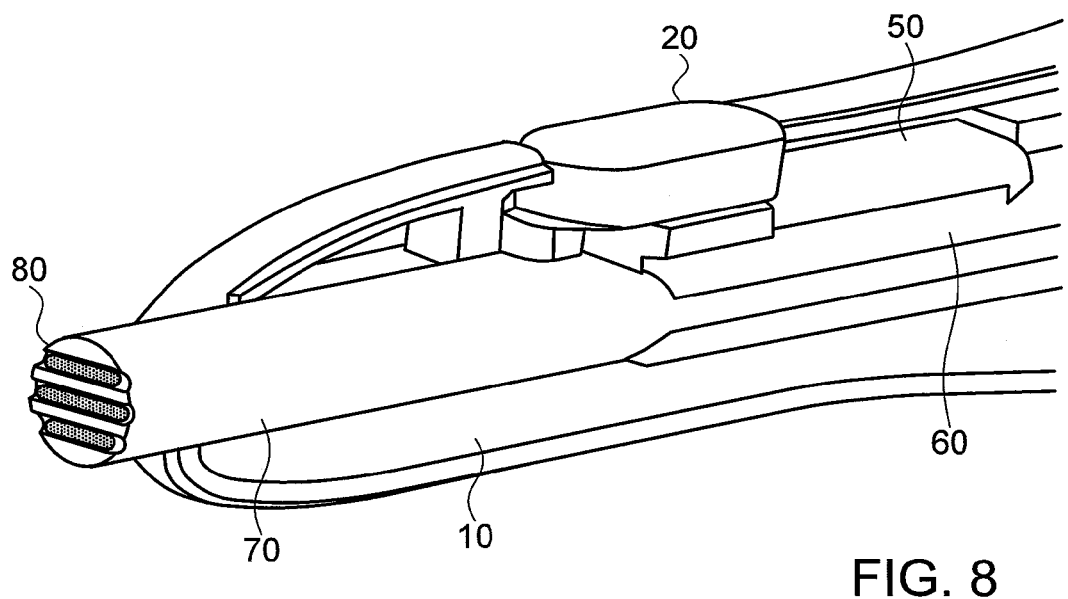
FIG. 8 is a cross-sectional illustration of the distal end of the applicator from FIG. 2 in which a liquid medicament is confined by capillary forces on the surface of dispenser 80.

FIG. 8 illustrates a cross-sectional view of a distal portion of applicator 100. Housing 10 is provided with an actuating button 20, drawing bar 50, rack 60, container 70 and dispenser 80. Container 70 is in fluid communication with dispenser 80. Upon pressing actuating button 20 a predetermined volume of the liquid medicament is discharged to the surface of dispense 80 where it is retained by capillary forces, as described hereinabove.

Figure 9:
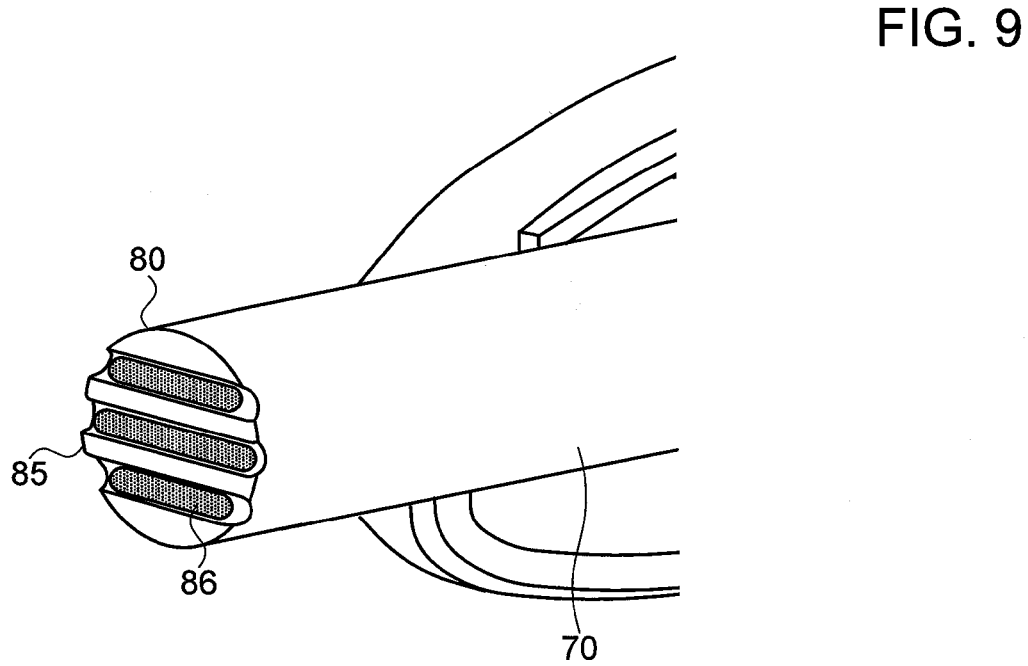
FIG. 9 is a cross-sectional illustration of the distal end of the applicator from FIG. 8 in which liquid medicament 86 is confined by capillary forces within structures 85 on the surface of dispenser 80.

FIG. 9 illustrates an enlarged view of dispenser 80 and structures 85 for retaining liquid medicament 86. Dispenser 80 has a surface area which is preferably ranges between about 1 mm$^2$ to about 100 mm$^2$, more preferably about 12 mm$^2$. The shape of dispenser 80 surface area is preferably rounded or curved for fitting a typical skin lesion.

Structure 85 is sized and configured for holding a predetermined volume of liquid medicament 86 via capillary forces, as described hereinabove. Suitable structures can be, for example, grooves, channels, or cavities. Each structure 85 includes at least one fluid conduit for enabling communication of fluid from container 70 to structures 85.

Dispenser 80 is made of rigid and non-deformable material as described hereinabove. In some embodiments the surface of dispenser 80 is sufficiently abrasive for enabling abrading or disrupting at least a portion of a skin lesion epidermis when pressure is applied; such abrasion/disruption can improve penetration of the medicament into skin lesion tissue.

The applicator of the present invention is particularly suitable for treating skin lesions.

Thus, according to another aspect of the present invention there is provided a method of treating a skin lesion of a subject in need thereof. The method includes the steps of: (i) communicating a predetermined volume of a liquid medicament from a container to a fluidly-coupled dispenser having a plurality of structures for retaining the predetermined volume of a liquid medicament; and (ii) contacting the dispenser with the skin lesion thereby delivering at least a part of the predetermined volume of the liquid medicament to the skin lesion.

As used herein the phrase "treating a skin lesion" refers to ablating and preferably separating the skin lesion from its base tissue.

As used herein the phrase "a subject in need thereof" refers to a mammal, preferably a human, having a skin lesion.

Following delivery of the medicament to the surface of the skin lesion, the dispenser is pressed on the treated skin lesion to facilitate tissue penetration of a therapeutically effective volume of the liquid medicament. Delivery of the medicament into the skin lesion tissue is preferably repeated several times, until the treated lesion appears to be at the same level (i.e., not raised above) with the surrounding healthy skin tissue.

The phrase "therapeutically effective volume" used herein refers to a volume of medicament which is sufficient to cause ablation and separation of the skin lesion from its base tissue.

As used herein the term "about" refers to ±10%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An applicator for administration of a medicament for treatment of a skin lesion, comprising:
    (a) a container containing a liquid medicament including trichloroacetic acid and being in fluid communication with a dispenser, said dispenser having an abrasive surface for abrading at least a portion of the skin lesion and having a plurality of non-deformable structures being configured for retaining a predetermined volume of said liquid medicament including trichloroacetic acid for ablation of the skin lesion; and
    (b) a mechanism configured for actuating release of about 1 µL to about 100 µL said liquid medicament from said container to said dispenser;
    wherein said plurality of non-deformable structures are configured for trapping and retaining about 1 µL to about 100 µL of said liquid medicament delivered thereto from said container such that said liquid medicament is only releasable from said plurality of non-deformable structures solely via capillary forces upon contact of said plurality of non-deformable structures with a skin region, said plurality of non-deformable structures being configured such that said contact and release of said liquid medicament does not expose skin tissue surrounding said skin region to said liquid medicament, said non-deformable structures include at least one fluid conduit communicating between said container and said dispenser, said non-deformable structures take the form of grooves, channels or cavities, said dispenser is configured to facilitate penetration of the said liquid medicament into the skin lesion.

2. The applicator of claim 1, wherein said plurality of non-deformable structures are configured for retaining said predetermined volume of said liquid medicament via capillary forces.

3. The applicator of claim 2, wherein delivering at least said part of said predetermined volume of said liquid medicament to said surface upon contact therewith is effected via capillary transfer.

4. The applicator of claim 1, wherein said plurality of non-deformable structures are grooves or cavities.

5. The applicator of claim 1, wherein said predetermined volume of said liquid medicament is about 5 µL.

6. The applicator of claim 1, wherein said container is a deformable container.

7. The applicator of claim 1, wherein said medicament further includes formic acid.

8. A method of treating a skin lesion comprising:
    (a) communicating a predetermined volume of a liquid medicament wherein said dispenser including trichloroacetic acid from a container to a fluidly-coupled dispenser having a plurality of non-deformable structures configured for retaining said predetermined volume of a liquid medicament having an abrasive surface for abrading at least a portion of the skin lesion when moved thereagainst; and
    (b) contacting said dispenser with the skin lesion, abrading at least a portion of said skin thereby disrupting a lesion surface and delivering at least a part of said predetermined volume of said liquid medicament into the skin lesion while not exposing skin tissue surrounding said skin lesion to said medicament.

9. The method of claim 8, wherein said plurality of non-deformable structures are configured for retaining said predetermined volume of a liquid medicament via capillary forces.

10. The method of claim 9, wherein said delivering is effected via capillary transfer.

11. The method of claim 10, further comprising forcibly pressing said dispenser on said skin lesion to thereby facilitate delivery of said medicament into said skin lesion tissue.

12. The method of claim 8, wherein said plurality of non-deformable structures are grooves or cavities.

13. The method of claim 8, wherein said skin lesion is a benign or a malignant skin lesion.

14. The method of claim 8, wherein said skin lesion is selected from a group consisting of seborrheic keratosis, actinic keratosis, intradermal nevus, verucae, condylomata acuminata, seborrheic dermatitis, atopic dermatitis, eczema, hyperkeratosis, acne (acne vulgaris) and psoriasis.

* * * * *